US009364157B2

(12) United States Patent  
Lu et al.

(10) Patent No.: US 9,364,157 B2  
(45) Date of Patent: Jun. 14, 2016

(54) APPARATUS BASED ON IMAGE FOR DETECTING HEART RATE ACTIVITY AND METHOD THEREOF

(71) Applicant: INDUSTRIAL TECHNOLOGY RESEARCH INSTITUTE, Hsinchu (TW)

(72) Inventors: Tung-Hung Lu, Yilan County (TW); Hui-Chen Ku, Zhubei (TW); Rong-Rong Chen, Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 168 days.

(21) Appl. No.: 14/243,110

(22) Filed: Apr. 2, 2014

(65) Prior Publication Data

US 2015/0131879 A1    May 14, 2015

(30) Foreign Application Priority Data

Nov. 14, 2013   (TW) .............................. 102141509 A

(51) Int. Cl.
| | |
|---|---|
| G06K 9/00 | (2006.01) |
| A61B 5/024 | (2006.01) |
| A61B 5/00 | (2006.01) |
| G06T 7/20 | (2006.01) |

(52) U.S. Cl.
CPC ................ *A61B 5/024* (2013.01); *A61B 5/004* (2013.01); *G06T 7/206* (2013.01); *G06T 2207/10024* (2013.01); *G06T 2207/20056* (2013.01); *G06T 2207/30048* (2013.01)

(58) Field of Classification Search
CPC .... A61B 5/024; A61B 2676/00; G06K 9/624; G06T 2207/10024; G06T 2207/30048
See application file for complete search history.

(56) References Cited

U.S. PATENT DOCUMENTS

| | | | | |
|---|---|---|---|---|
| 8,360,986 B2 * | 1/2013 | Farag | ................. | A61B 5/02055 |
| | | | | 600/500 |
| 8,897,522 B2 * | 11/2014 | Mestha | ..................... | A61B 5/02 |
| | | | | 382/128 |
| 8,902,045 B1 * | 12/2014 | Linn | ....................... | G06F 21/32 |
| | | | | 340/5.53 |

(Continued)

OTHER PUBLICATIONS

Poh, Ming-Zher, Daniel J. McDuff, and Rosalind W. Picard. "Noncontact, automated cardiac pulse measurements using video imaging and blind source separation." Optics Express 18 (2010): 10762. © 2011 Optical Society of America. p. 1-14.*

(Continued)

*Primary Examiner* — Gandhi Thirugnanam  
(74) *Attorney, Agent, or Firm* — Rabin & Berdo, P.C.

(57) ABSTRACT

An apparatus and method based on image for detecting heart rate activity is provided. The method includes: obtaining a plurality of color images; based on a complexion target condition, defining a target region; performing color composition analysis on the target region to obtain red channel signal, green channel signal and blue channel signal, respectively; performing independent component analysis on separate red, green and blue channel signals to obtain separate first independent component signal, second independent component signal and third independent component signal; performing frequency domain transform, signal energy computation and signal optimization processes on separate first, second and third independent component signals to obtain a filter signal, comparing filter signal based on a pre-set condition to determine if target region belonging to a human, and performing a physiological information analysis.

36 Claims, 9 Drawing Sheets

(56) References Cited

U.S. PATENT DOCUMENTS

| | | | | |
|---|---|---|---|---|
| 8,965,090 | B1* | 2/2015 | Khachaturian | A61B 5/0261 382/128 |
| 9,020,185 | B2* | 4/2015 | Mestha | A61B 5/0075 382/100 |
| 9,036,877 | B2* | 5/2015 | Kyal | A61B 5/7225 382/107 |
| 9,185,353 | B2* | 11/2015 | Mestha | H04N 7/18 |
| 2002/0183640 | A1* | 12/2002 | Bjorling | A61B 5/04023 600/517 |
| 2009/0135188 | A1 | 5/2009 | Ding et al. | |
| 2011/0251493 | A1* | 10/2011 | Poh | G06K 9/00255 600/477 |
| 2012/0195473 | A1* | 8/2012 | De Haan | G06T 7/20 382/107 |
| 2012/0250957 | A1* | 10/2012 | Syeda-Mahmood | G06T 7/0016 382/128 |
| 2013/0085407 | A1* | 4/2013 | Siejko | A61B 7/04 600/528 |
| 2013/0343614 | A1* | 12/2013 | Kyal | G06K 9/0057 382/107 |
| 2013/0345568 | A1* | 12/2013 | Mestha | A61B 5/7235 600/473 |
| 2013/0345569 | A1* | 12/2013 | Mestha | A61B 5/0044 600/473 |
| 2015/0131879 | A1* | 5/2015 | Lu | A61B 5/004 382/128 |

OTHER PUBLICATIONS

Poh, Ming-Zher et al, "Advancements in Noncontact, Multiparameter Physiological Measurements Using a Webcam", Jan. 2011, IEEE Transactions on Biomedical Engineering, vol. 58 No. 1, p. 7-11.*

M. Lewandowska et al, "Measuring Pulse Rate with a Webcam—A Non-contact Method for Evaluating Cardiac Activity", 2011, Proceedings of the Federated Conference on Computer Science and Information Systems, p. 405-410.*

H. Wu et al., "Eulerian Video Magnification for Revealing Subtle Changes in the World", 2012, ACM Transactions on Graphics, p. 1-8.*

Poh et al., Advancements in noncontact, multiparameter physiological measurements using a webcam, IEEE Conference Publications(Biomedical Engineering, IEEE Transactions on), 2011, p. 7~p. 11.

Poh et al., Non-contact, automated cardiac pulse measurements using video imaging and blind source separation, MIT Open Access Articles (http://hdl.handle.net/1721.1/66243), 2010, p. 10762-p. 10774.

Wu et al., Eulerian video magnification for revealing subtle changes in the world, ACM Transactions on Graphics (TOG), 2012, p. 65-p. 73.

Lewandowska et al., Measuring pulse rate with a webcam—A non-contact method for evaluating cardiac activity, IEEE Conference Publications (InComputer Science and Information Systems (FedCSIS), 2011 Federated Conference on. IEEE.), 2011, p. 405-p. 410.

Ahmed Elgammal, Crystal Muang and Dunxu Hu, Skin Detection—a Short Tutorial, Aug. 27, 2009, pp. 1-10, Encyclopedia of Biometrics by Springer-Verlag Berlin Heidelberg 2009.

Wang et al. Face live detection method based on physiological motion analysis, Tsinghua Science & Technology, 2009, 14(6), pp. 685-690.

Pan et al, Liveness detection for face recognition, INTECH Open Access Publisher. 2008, pp. 109-124.

Bhatia et al., Alive human body detection system using an autonomous mobile rescue robot, N. In India Conference (INDICON), 2011 Annual IEEE, Dec. 2011, pp. 1-5. IEEE.

\* cited by examiner

APPARATUS BASED ON IMAGE FOR DETECTING HEART RATE ACTIVITY AND METHOD THEREOF

CROSS-REFERENCE TO RELATED APPLICATION

The present application is based on, and claims priority form, Taiwan Patent Application No. 102141509, filed Nov. 14, 2013, the disclosure of which is hereby incorporated by reference herein in its entirety.

TECHNICAL FIELD

The technical field generally relates to an apparatus based on image for detecting heart rate activity and method thereof.

BACKGROUND

As demands of medical care and technological development, the electronic, information and communication technologies are widely applied to medical care. Take caring of infants or patients as an example. The monitoring of cardio activity is an important part. In infants and young children, for example, to monitor the heart rate and respiratory activity can significantly prevent the occurrence of heart activity disorders in infants, which often resulting in the subsequent chain of health problems and even sudden death crisis. Therefore, baby monitors used in monitoring and caring is common. Also, the medical or physiological monitoring equipments which are commonly used in the clinical care of bedridden patients are mostly contact-based monitoring devices to capture breathing and heartbeat signals of the patient, such as, using detection electrodes attached to the chest skin and using monitors, heart rate band, or finger-type detection equipment. However, for contact-based detection, a disadvantage is the possible discomfort on the skin. In addition, the clinical monitoring equipments are expensive and do not meet the demand for home care use. There are other care products designed for the detection of human respiration and heartbeat caused by slight vibration. The principle is based on a mattress or lying sensing element mounted to detect the slight vibrations transmitted to a measuring and monitoring apparatus. These technologies still have a low resolution problem, and are vulnerable to environmental vibration noise interference.

Massachusetts Institute of Technology (MIT) disclosed a method of detecting human heartbeat using dynamic images (pulse). This approach, after face detection, uses image-processing algorithm to detect the changes in skin color features invisible to naked eyes in continuous image of a human face, for example, RGB values in the face image, amplify the signal, filter out the noise, and use Blind Source Separation analysis to distinguish slight changes in facial blood flow under various states of the human heart rates, and then estimates a heart rate. As such, a non-contact detection can be obtained. Similarly, Gdańsk University of Technology, Poland research team has also made a similar image computing technologies to detect a heartbeat.

In practical application, the current image-based technology for detecting heart rate activity usually has the following disadvantages. First, the existing image detection technology demands the monitored objects to be in certain posture or stability, for example, a front continuous stationary posture. In particular, the existing technology typically uses human face as the image acquisition target. However, the infant's actions and behavior are usually difficult to control and meet the basic requirements of face recognition; therefore, the image is difficult for use in this type of detection technology relying on face recognition. Furthermore, infant cardiopulmonary function, physiological state and behavior are very different from the adults. To adopt cardiopulmonary imaging techniques to monitor the physiological status of infants and young children, there are still many technical barriers to be overcome. Finally, in order to achieve accurate detection of the target, the use of face recognition technology sensing devices (i.e., cameras) requires relatively higher sensitivity and resolution, thereby increasing the cost for equipment purchases.

In response to these problems, Rutgers University research team (Elgammal) proposed to replace face detection with the human skin color detection technology. However, the existing techniques for human skin color detection have an error rate as high as 15-30%, and are easy to mistake non-human object with color similar to real skin color for human, resulting in false alarm, interference calculation and interpretation. Furthermore, the known skin color detection techniques treat disconnected regions of pixels as different monitored targets, and can not determine the relevance between disconnected skin color regions, or the relevance between each skin color region and the monitored target, which often results in gaps between information processing and interpretation.

In summary, the known image-based monitoring techniques still have many problems to overcome.

SUMMARY

An exemplary embodiment describes an image-based method for detecting heart rate activity, including: obtaining a plurality of color images of a monitored target; executing a target area detection process targeting the color images, wherein the target area detection process performing computation analysis on the color images to define a target area in the monitored target in the color image according to a predefined skin color target condition; performing a color image composition analysis on the target area, wherein the color image composition analysis performing statistic computation for a red channel, a green channel and a blue channel of the target area to obtain a red channel signal, a green channel signal and a blue channel signal; based on an independent component analysis method, performing computation on the red channel signal, the green channel signal and the blue channel signal to obtain a first independent component signal, a second independent component signal, and a third independent component signal; performing a frequency domain transform process, a signal energy computation process and a signal fitness process for the first independent component signal, the second independent component signal, and the third independent component signal to obtain a filtered signal; based on a predefined condition, performing comparison on the filtered signal to confirm the monitored target as a real human and provide an analysis instruction accordingly; and based on the analysis instruction, executing a physiological information analysis process.

Another embodiment describes an image-based method for detecting heart rate activity, including: obtaining a plurality of color images of a plurality of monitored targets; executing a target area detection process targeting the color images, wherein the target area detection process performing computation analysis on the color images to define a plurality of target areas in the monitored target in the color image according to a predefined skin color target condition; performing a color image composition analysis on each of the plurality of target areas, wherein the color image composition analysis performing statistic computation for a red channel, a green channel and a blue channel of each of the target areas to obtain a red channel signal, a green channel signal and a blue channel signal; based on an independent component analysis method, performing computation on the red channel signal, the green channel signal and the blue channel signal of each of the target areas to obtain a first independent component signal, a second independent component signal, and a third independent component signal; performing a frequency domain transform process, a signal energy computation process and a signal fitness process for the first independent component signal, the second independent component signal, and the third independent component signal of each of the target areas to obtain a filtered signal; based on a first pre-defined condition, performing comparison on the filtered signal of each of the target areas to confirm the filtered signal of each of target areas as a real human signal; based on a second—pre-defined condition, performing comparison respectively on each filtered signal of each of the target areas to identify relevance among each of the target areas to confirm whether each of the target areas belonging to a real human and provide an analysis instruction accordingly; and based on the analysis instruction, executing a physiological information analysis process.

Another exemplary embodiment describes an image-based apparatus for detecting heart rate activity, including: a detecting unit, configured to obtain a plurality of color images of a monitored target; a memory unit, coupled to the detecting unit, configured to store the color images obtained by the detecting unit; and a processor, coupled to the memory unit, wherein the processor further including: a target area defining module, configured to execute a target area detection process targeting the color images, wherein the target area detection process performing computation analysis on the color images to define a target area in the monitored target in the color image according to a predefined skin color target condition; a color image composition analysis module, configured to perform a color image composition analysis on the target area, wherein the color image composition analysis performing statistic computation for a red channel, a green channel and a blue channel of the target area to obtain a red channel signal, a green channel signal and a blue channel signal; an independent component analysis module, based on an independent component analysis method, configured to perform computation on the red channel signal, the green channel signal and the blue channel signal to obtain a first independent component signal, a second independent component signal, and a third independent component signal; a signal processing module, configured to perform a frequency domain transform process, a signal energy computation process and a signal fitness process for the first independent component signal, the second independent component signal, and the third independent component signal to obtain a filtered signal; a comparison module, based on a pre-defined condition, configured to perform comparison on the filtered signal to confirm the monitored target as a real human and provide an analysis instruction accordingly; and a physiological information analysis module, based on the analysis instruction, configured to execute a physiological information analysis process.

Another embodiment describes an image-based apparatus for detecting heart rate activity, including: a detecting unit, configured to obtain a plurality of color images of a plurality of monitored targets; a memory unit, coupled to the detecting unit, configured to store the color images obtained by the detecting unit; a processor, coupled to the memory unit, wherein the processor further including: a target area defining module, configured to execute a target area detection process targeting the color images, wherein the target area detection process performing computation analysis on the color images to define a plurality of target areas in the monitored target in the color image according to a predefined skin color target condition; a color image composition analysis module, configured to perform a color image composition analysis on each of the plurality of target areas, wherein the color image composition analysis performing statistic computation for a red channel, a green channel and a blue channel of each of the target areas to obtain a red channel signal, a green channel signal and a blue channel signal; an independent component analysis module, based on an independent component analysis method, configured to perform computation on the red channel signal, the green channel signal and the blue channel signal of each of the target areas to obtain a first independent component signal, a second independent component signal, and a third independent component signal; a signal processing module, configured to perform a frequency domain transform process, a signal energy computation process and a signal fitness process for the first independent component signal, the second independent component signal, and the third independent component signal of each of the target areas to obtain a filtered signal; a comparison module, based on a first pre-defined condition, configured to perform comparison on the filtered signal of each of the target areas to confirm the filtered signal of each of target areas as a real human signal; a relevance analysis module, based on a second pre-defined condition, configured to perform comparison respectively on each filtered signal of each of the target areas to identify relevance among each of the target areas to confirm whether each of the target areas belonging to a real human and provide an analysis instruction accordingly; and a physiological information analysis module, based on the analysis instruction, configured to execute a physiological information analysis process.

The foregoing will become better understood from a careful reading of a detailed description provided herein below with appropriate reference to the accompanying drawings.

BRIEF DESCRIPTION OF THE DRAWINGS

The embodiments can be understood in more detail by reading the subsequent detailed description in conjunction with the examples and references made to the accompanying drawings, wherein.

DETAILED DESCRIPTION OF THE DISCLOSED EMBODIMENTS

Figure 1:
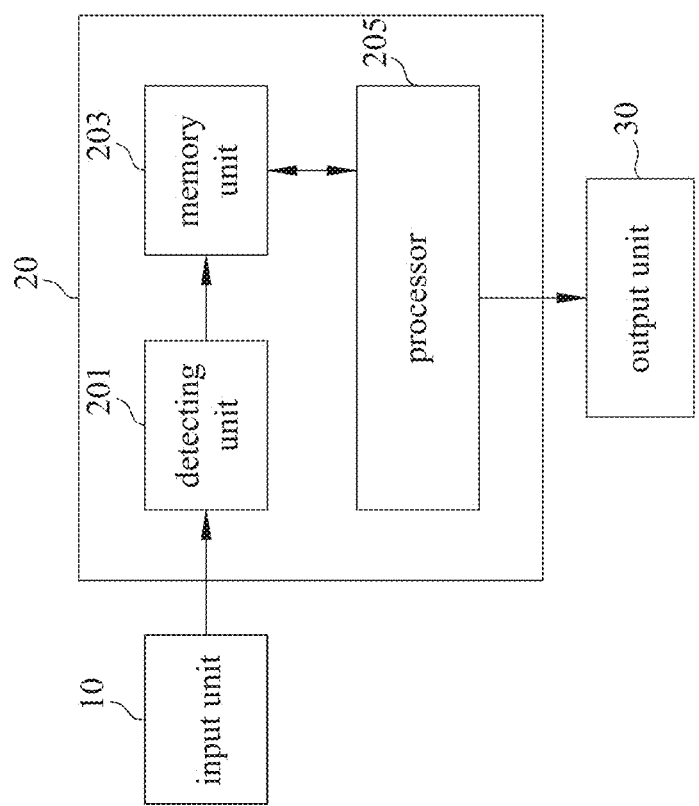
FIG. 1 shows a schematic view of the structure of an image-based apparatus for detecting heart rate activity in accordance with an exemplary embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The term coupling refers to any direct or indirect connection means. For example, when a first device is described as coupled to a second device, it means that the first device is either directly connected to the second device or the first device is indirectly connected to the second device through another device or some connection means. In addition, the heart rate activity described in the disclosure broadly refers to the physiological values of the heart beat of a human body, which can be computed to obtain a plurality of physiological parameters including, but not restricted to, heart beat rate. Specifically, when a user inputs or set other physiological parameters in advance, the image-based apparatus for detecting heart rate activity in the present disclosure can further perform physiological information analysis related to heart rate activity in accordance with related parameter.

FIG. 1 shows a schematic view of the structure of an image-based apparatus 20 for detecting heart rate activity, coupled to an input unit 10 and an output unit 30. The image-based apparatus 20 for detecting heart rate activity includes: a detecting unit 201, configured to obtain a plurality of color images of a monitored target; a memory unit 203, coupled to the detecting unit 201, configured to store the color images obtained by the detecting unit; and a processor 205, coupled to the memory unit 203, wherein the processor 205 performing image analysis based on the color images stored in the memory unit 203. The input unit 10 coupled to the image-based apparatus 20 for detecting heart rate activity can be an image detecting and recording equipment, for example, camera, digital recording equipment, webcam, and so on, operation equipment for instructing operation and inputting settings, information processing equipment; and the coupled output unit 30 can be a multimedia display equipment. Both are realized with known technologies, and thus no detailed description is required in the disclosure.

The detecting unit 201 is to detect the location of the monitored target and dynamic image change in the specific surroundings (depending on the field of view of the detecting equipment), as well as to obtain continuous color images for subsequent analysis to monitor the dynamic changes of physiological information of the monitored target. The monitored target refers to persons to be monitored for physiological parameters of heart rate activity, such as heart beat, and includes, but not restricted to, babies, toddlers and patients. However, in the present disclosure, babies are used as preferred embodiment to explain the features and advantages of the present disclosure.

The detecting unit 201 is coupled to the input unit 10 so that users can input parameter settings or adjust the process through the instruction interface provided by the input unit 10. The memory unit 203 is coupled to the detecting unit 201, for storing the continuous color images obtained by the detecting unit 201. The memory unit 203 can be realized by any memory element able to store digital image data and able to support the processor 205 to access and process the image data. Therefore, both non-volatile memory, such as ROM or flash memory, and volatile memory, such as static or dynamic RAM, are applicable to the present disclosure.

The processor 205 is coupled to the memory unit 203. The processor 205 first distinguishes target areas (i.e., the exposed skin areas of the baby) on the color images stored in the memory unit 203. The processor 205 then performs color image analysis. Based on the analysis result from the color images, the processor 205 determines whether a skin area of a real human is included in the color image and excludes the non-human images to avoid erroneous detection. In addition, when a plurality of target areas is included in the color image, the processor 205 also determines the relevance of the target areas based on the image analysis result, i.e., to determine whether each of the target areas belongs to a same baby or a different baby and grouped accordingly. After obtaining the above information, the processor 205 perform further computation to obtain the physiological parameters related to the heart rate activity based on the image analysis result. After completing the above analysis, the processor 205 integrates the information following the detection parameters or process inputted by the user and transmits the information to the output unit 30 coupled to the processor 205 so that the user can observe the monitored information or related warning messages to monitor the heart rate activity of the babies.

Figure 2:
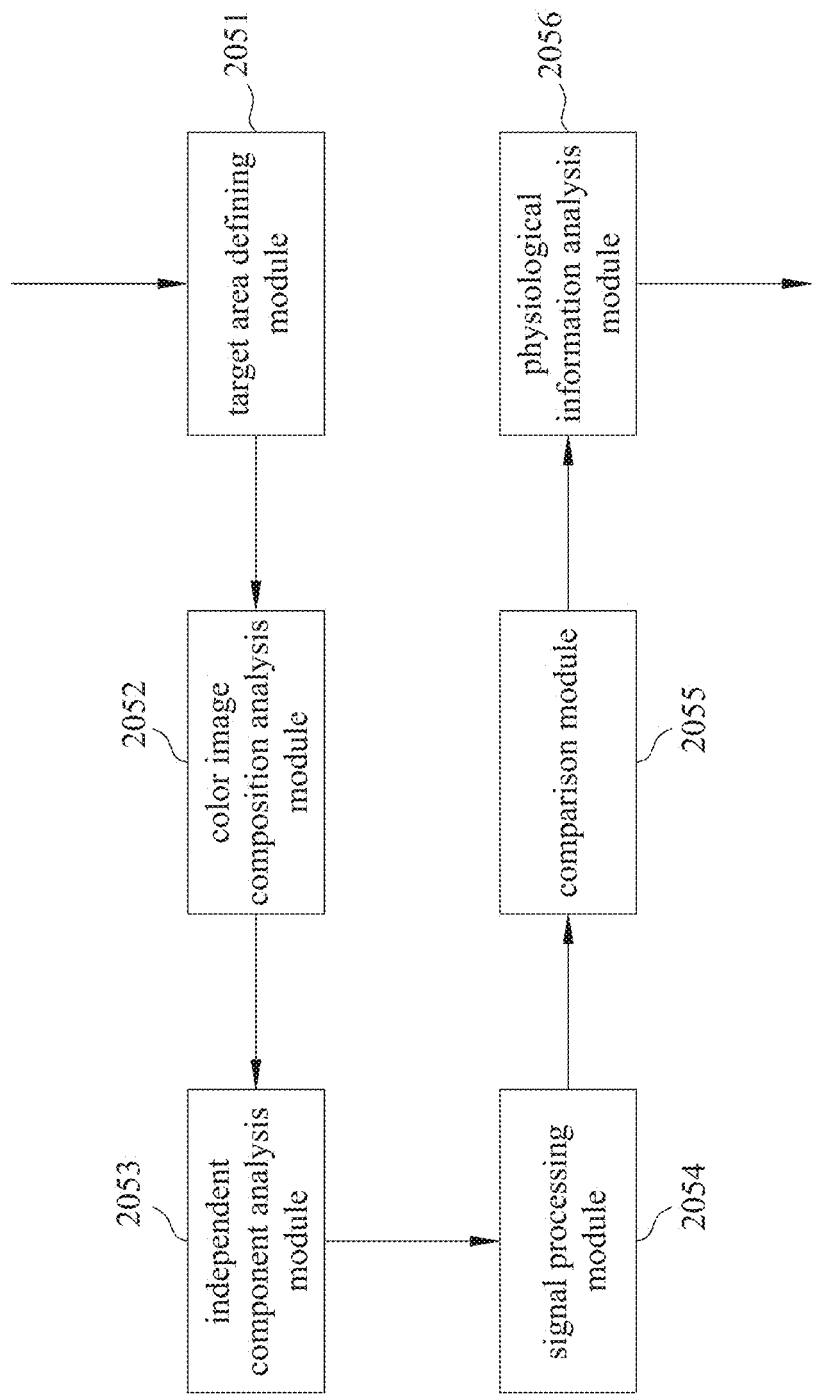
FIG. 2 shows a schematic view of the first embodiment of the structure of the processor in FIG. 1 in accordance with an embodiment.

Accordingly, FIG. 2 shows a schematic view of the first embodiment of the structure of the processor 205 in accordance with an embodiment. As shown in FIG. 2, the processor 205 further includes: a target area defining module 2051, configured to execute a target area detection process targeting the color images, wherein the target area detection process performing computation analysis on the color images to define a target area in the monitored target in the color image according to a predefined skin color target condition; a color image composition analysis module 2052, configured to perform a color image composition analysis on the target area, wherein the color image composition analysis performing statistic computation for a red channel, a green channel and a blue channel of the target area to obtain a red channel signal, a green channel signal and a blue channel signal; an independent component analysis module 2053, based on an independent component analysis method, configured to perform computation on the red channel signal, the green channel signal and the blue channel signal to obtain a first independent component signal, a second independent component signal, and a third independent component signal; a signal processing module 2054, configured to perform a frequency domain transform process, a signal energy computation process and a signal fitness process for the first independent component signal, the second independent component signal, and the third independent component signal to obtain a filtered signal; a comparison module 2055, based on a pre-defined condition, configured to perform comparison on the filtered signal to confirm the monitored target as a real human and provide an analysis instruction accordingly; and a physiological information analysis module 2056, based on the analysis instruction, configured to execute a physiological information analysis process.

Figure 3:
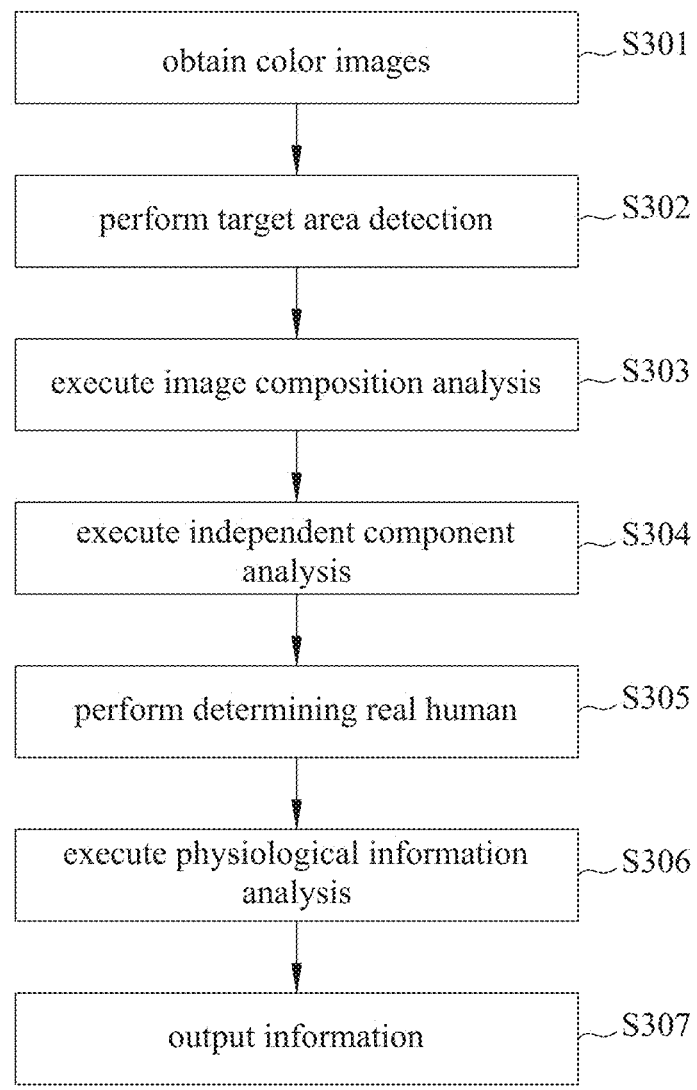
FIG. 3 shows a flowchart of the method for detecting heart rate activity executed by the processor in FIG. 2 in accordance with an exemplary embodiment.

FIG. 3 shows a flowchart of the method for detecting heart rate activity executed by the processor 205 of the image-based apparatus 20 for detecting heart rate activity in accordance with an exemplary embodiment. As shown in FIG. 3, step S301 is to obtain color images, step S302 is to perform target area detection, step S303 is to execute image composition analysis, step S304 is to execute independent component analysis, step S305 is to perform determining real human, step S306 is to execute physiological information analysis and step S307 is to output detection result through the output unit.

Accordingly, in step S301, the target area defining module 2051 execute a target area detection process targeting the color images stored in the memory unit 203, wherein the target area detection process performing computation analysis on the color images to define a target area, such as, exposed skin area of a baby, in the monitored target in the color image according to a predefined skin color target condition. The predefined target skin color condition is the condition defined based on the characteristics (such as, pixel location and color information included in the pixels) of the skin color pixels of all races. Based on the target color condition, a pixel area matching the skin color pixel characteristics is viewed as a skin color target and the area wherein the skin color target is distributed is defined as a target area. The theory and the technique of the above skin color pixel characteristics is known to related technical field and will not be described in details here.

Hence, the present disclosure directly defines the target area based on skin color characteristics, instead of the conventional facial recognition. As such, the problems resulted from facial recognition technique are avoided. The skin color based technique is appropriate to babies as the movements and activities of babies are difficult to control. Also, the technique can be applied to monitoring sleeping babies whose full frontal face is not shown, wherein the facial recognition technique cannot be used.

In step S302, the color composition analysis module 2052 performs a color image composition analysis on the target area defined in step S301, wherein the color image composition analysis performing statistic computation for a red channel (R), a green channel (G) and a blue channel (B) of the target area. In practice, the color composition analysis module 2052 can directly perform statistics computation on all colors of a color image, or perform statistic computation after separating each color channel of a color image. After the color composition analysis module 2052 completes statistics computation on the composition of each color (including, luminance change of each color, such as mean luminance, maximum luminance or minimum luminance; or other quantifiable statistics of each color channel), the amount of each color channel can be obtained so as to obtain a red channel signal, a green channel signal and a blue channel signal.

In step 303, the independent component analysis module 2053 performs computation on the red channel signal, the green channel signal and the blue channel signal according to an independent component analysis (ICA) method. ICA method is a known statistic analysis algorithm, and details will be omitted here. In short, ICA method is an analysis method able to perform linear transformation on a hybrid data or signal to separate into independent statistic signal source. The preferred embodiment uses FastICA, which is an ICA-based method, to accelerate signal analysis and improve signal separation result. Therefore, after processing the red channel signal, the green channel signal and the blue channel signal with ICA computation, a first independent component signal, a second independent component signal, and a third independent component signal are obtained from the above hybrid signal.

In step S304, the signal processing module 2054 perform the following signal processing processes in order on the first independent component signal, the second independent component signal, and the third independent component signal: a frequency domain transform process, a signal energy computation process and a signal fitness process, described in details as follows.

Accordingly, the frequency domain transform process is to transform the aforementioned three independent component signals into frequency domain so that a first frequency domain signal, a second frequency domain signal and a third frequency domain signal can be obtained from the first independent component signal, the second independent component signal, and the third independent component signal respectively. The frequency domain transform process may include any known computation means, such as, Fourier Transform, which is a preferred embodiment in the present disclosure.

On the other hand, the signal energy computation process is to compute signal energy of the aforementioned frequency domain signals (i.e., the first frequency domain signal, the second frequency domain signal and the third frequency domain signal), and a preferred embodiment includes, but not restricted to, Euclidean Norm Algorithm. Then, according to the signal energy of each frequency domain signal, a maximum signal energy is selected and backtracked to select the corresponding independent component signal, which is called target independent component signal, for subsequent analysis target.

Then, a signal fitness process is performed on the above target independent component signal. The signal fitness process may include any know computation means, and a preferred embodiment includes, but not restricted to, a smoothing processing method and a filtering processing method. After completing the signal fitness process, the filtered signal of each target component signal can be obtained. That is, each target area generates a corresponding filtered signal.

In order to determine the filtered signal of each target area to obtain correct and effective analysis, the signal processing module 2054 must further computed interpretation parameters derived from each filtered signal, including: signal parameters (such as, regularity parameter) corresponding to each filtered signal, for determining whether each target area is a real human signal or a false human signal to provide subsequent comparison and analysis.

In step S305, the comparison module 2055 performs comparison on each filtered signal corresponding to each target area to confirm whether each target area as a real human according to a first pre-defined condition. Specifically, when regularity parameter matches a default regularity value, the monitored target is determined as a real human baby; otherwise, a false signal and the signal source area not belonging to a real human bay. Therefore, when the color image detected by the detecting unit 201 only includes a single target area, the single target area can be directly determined whether belonging to a real human bay. When confirmed as a real human bay, an analysis instruction is provided accordingly and a physiological information analysis process can be performed on the filtered signal generated according to the target area.

Then, in step S306, the physiological information analysis module 2056 executes integrated analysis according to the analysis instruction provided by the comparison module 2055. The physiological information analysis module 2056 performs physiological information analysis on one or more babies. The theory of physiological information analysis is that the heart beat physiological information and blood flow condition are related and can be reflected in a tiny color change on the surface skin, and can be seen in the continuous series of color images. Therefore, by analyzing the color component changes in the continuous series of color images, the physiological information can be obtained. For example, the heme in the blood can absorb green light. Thus, by analyzing the change frequency of the color channel (pixel) in the image, the heart rate can be computed. Finally, in step S307, the analysis result is outputted through the output unit 30.

It should be noted that, in addition to perform physiological information analysis on babies, the aforementioned apparatus and method are also applicable to adults. Other applications include scenarios where facial recognition technique is not suitable, such as, head counts, body tracking, and so on.

It should also be noted that the order of the above steps is only a preferred embodiment. Thus, with the scope of the present disclosure, the user can add a step of adjusting the execution order of analysis computation depending on the application to improve the effectiveness of the embodiments of the disclosure.

Figure 4:
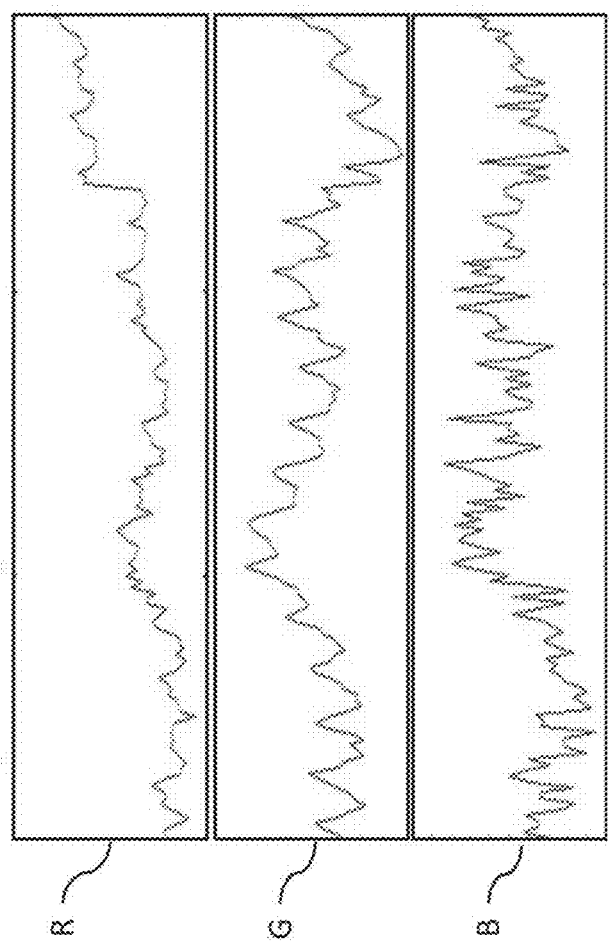
FIG. 4 shows a schematic view of statistics of red channel signal R, green channel signal G and blue channel signal B obtained after executing color composition analysis on the target skin area of the first embodiment in accordance with an exemplary embodiment.
Figure 5:
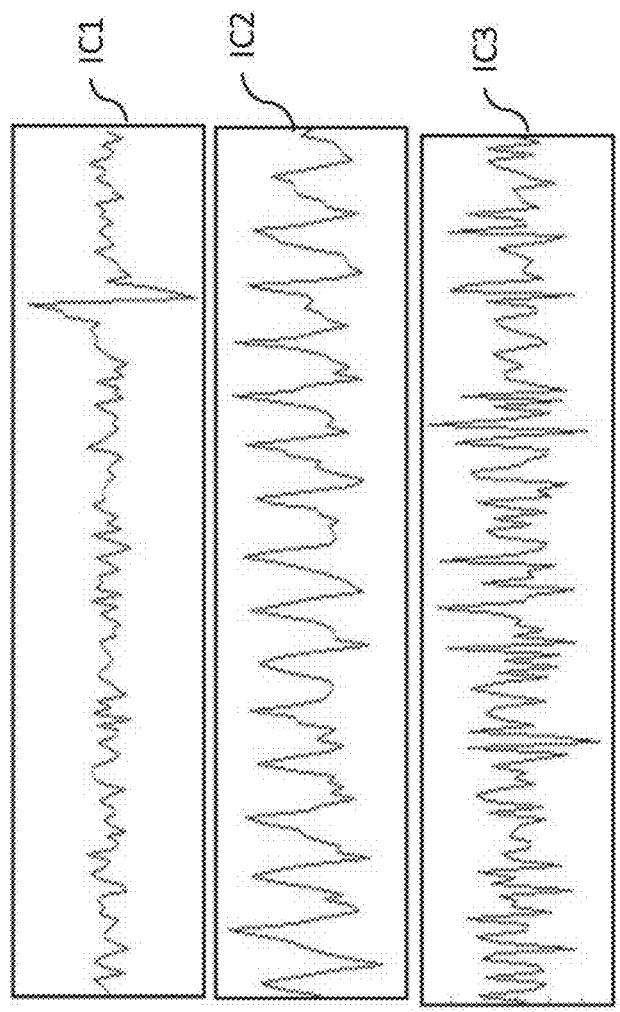
FIG. 5 shows a schematic view of analysis result of each independent signal component detected by the first embodiment in accordance with an exemplary embodiment.
Figure 6:
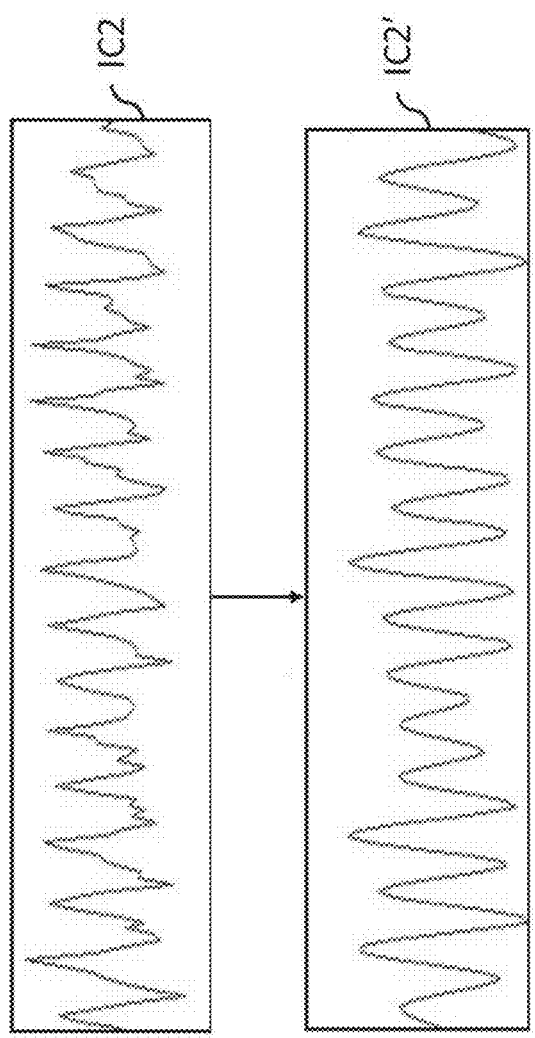
FIG. 6 shows a schematic view of signal processing on the second independent component of FIG. 5 of the first embodiment in accordance with an exemplary embodiment.

FIGS. 4-6 show intermediate results of a scenario according to an embodiment of the present invention. The first scenario is to monitor the heart rate activity of a single baby. The baby is wrapped in a blanket with only face exposed. The second scenario is to monitor the heart rate activity of a single baby, sleeping with a doll with skin color. FIG. 4 shows a schematic view of statistics of red channel signal R, green channel signal G and blue channel signal B obtained after executing color composition analysis on the target skin area of the first embodiment in accordance with an exemplary embodiment. FIG. 5 shows a schematic view of analysis result of each independent signal component detected by the first embodiment. FIG. 6 shows a schematic view of signal processing on the second independent component of FIG. 5, where the second independent component signal IC2 with maximum signal energy is selected after transformed by Fourier Transformation to frequency domain and completing Euclidean norm algorithm, followed by subsequent smoothing processing and filtering processing methods on the second independent component signal IC2 to obtain a corresponding filtered signal IC2'.

The experiment result of the present disclosure shows that, when executing step S305 for confirming real human, a regularity parameter is obtained by performing computation on a filtered signal generated by the skin color area, and the regularity parameter is positively proportional to the maximum signal energy of the filtered signal in frequency domain. Then, the regularity parameter is compared against a regularity default value, wherein a real human shows a higher regularity. Therefore, if the regularity parameter is higher than the regularity default value, the signal is determined as from a real human; otherwise, the signal is determined as false. For the first scenario, the regularity parameter measured for the facial area of the baby is 485.2, which is greater than the regularity default value 50; thus, a real human baby. For the second scenario, the regularity parameter measured for the facial area of the baby is 372.3, which is greater than the regularity default value 50; thus, a real human baby; while the regularity parameter measured for the skin-color doll is 35.3, which is less than the regularity default value 50; thus, not a real human baby.

Furthermore, according to the above real human confirmation, the comparison module 2055 generates an analysis instruction to instruct the performing of physiological information analysis of the filter signal of the facial area. For the first scenario, the facial area is determined as a real human and no other skin color area is present, hence the comparison module 2055 issues an analysis instruction to instruct the subsequent physiological information analysis of the facial area of the baby. For the second scenario, the facial area is determined as a real human and the skin-color doll is not a real human, hence the comparison module 2055 issues an analysis instruction to instruct the subsequent physiological information analysis of the facial area of the baby and discords the area of the skin-color doll. In other words, according of the above analysis step, for the facial area of the baby in the first and the second scenarios, step S304 uses the amplitude change speed of the selected filtered signal to compute the heart rate.

Figure 7:
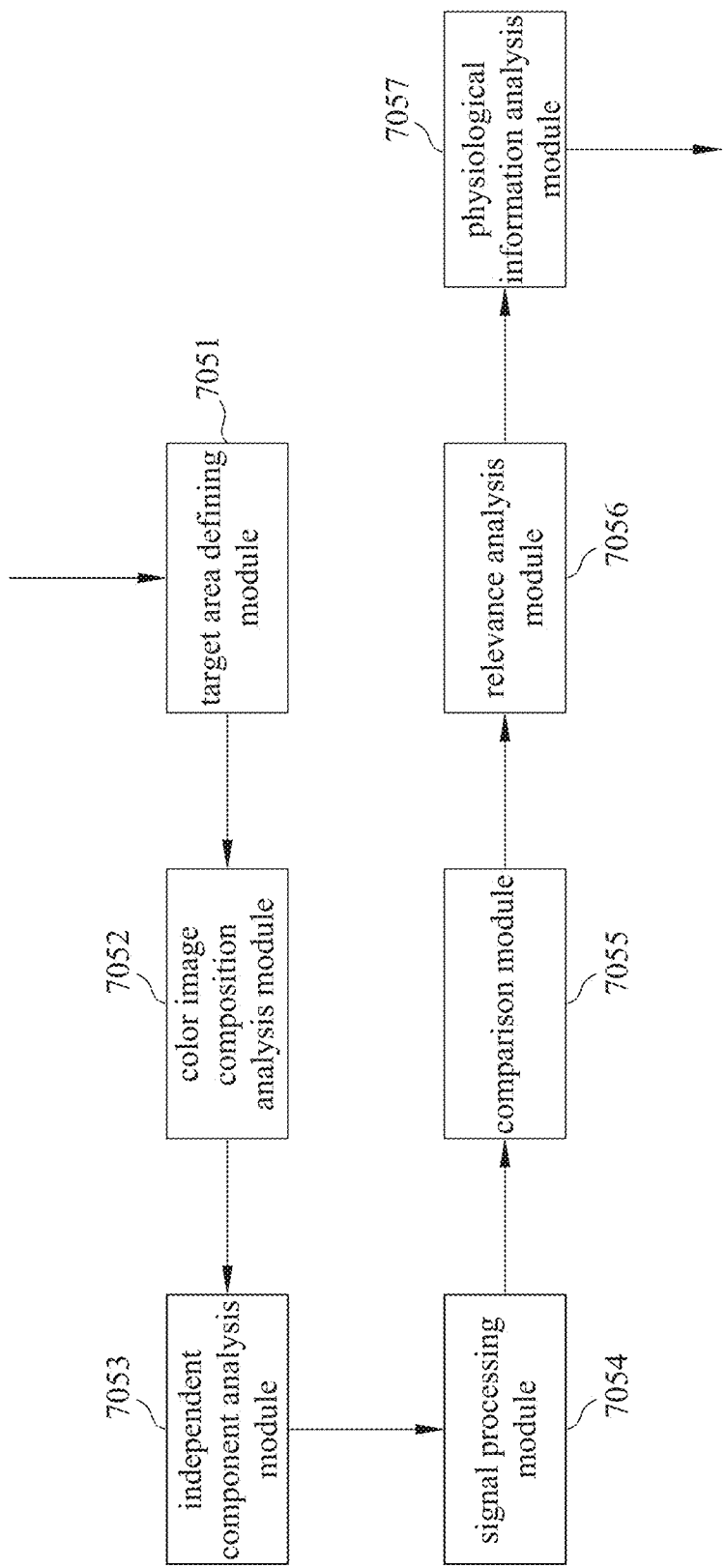
FIG. 7 shows a schematic view of the second embodiment of the structure of the processor in FIG. 1 in accordance with an embodiment.

FIG. 7 shows a schematic view of the second embodiment of the structure of the processor 205. In the present embodiment, the processor 205 further includes: a target area defining module 7051, a color image composition analysis module 7052, an independent component analysis module 7053, a signal processing module 7054, a comparison module 7055, a relevance analysis module 7056, and a physiological information analysis module 7057; wherein the target area defining module 7501, color image composition analysis module 7052, independent component analysis module 7053, comparison module 7055, and physiological information analysis module 7057 are the same as the target area defining module 2051, color image composition analysis module 2052, independent component analysis module 2053, comparison module 2055, and physiological information analysis module 2056 in the first embodiment in FIG. 2. Thus, the description of the functions of these modules will be omitted.

On the other hand, in addition to the functions of the signal processing module 2054, the signal processing module 7054 further includes: computing comparison parameter (waveform difference parameter) among the filtered signals, for identifying the relevance among the target areas to determine whether a plurality of target areas belonging to a same baby.

Then, the signal processing module 7054 sends the parameters (regularity parameter and waveform difference parameter) to the comparison module 7055 and the relevance analysis module 7056 respectively, such that the parameters are compared with a plurality of pre-defined conditions to obtain the correct signal for subsequent analysis; wherein the plurality of pre-defined conditions includes: a regularity default value and a waveform difference default value, for comparison against the regularity parameter and waveform difference parameter to determine whether the pre-defined conditions are matched.

As aforementioned, the comparison module 7055 compares each filtered signal corresponding to each target area based on a first pre-defined condition (i.e., regularity default value) to determine whether each target area is a real human signal (i.e., the signal is from a real human) to confirm that each target area belongs to a real human.

The difference between the present embodiment and the previous embodiment is that the relevance analysis module 7056 in the present embodiment can compare each filtered signals corresponding to each target area based on a second pre-defined condition (i.e., waveform difference default value) to determine the relevance among the target areas.

Figure 8:
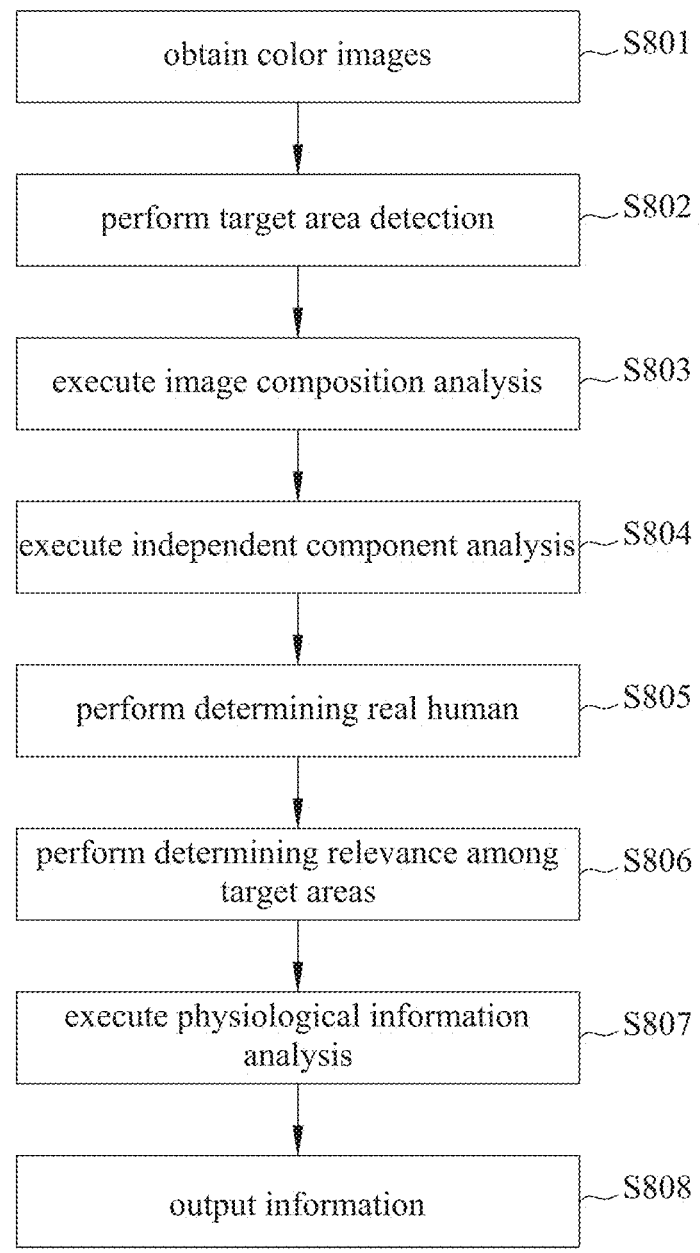
FIG. 8 shows a flowchart of the method for detecting heart rate activity executed by the processor in FIG. 7 in accordance with an exemplary embodiment.

FIG. 8 shows a flowchart of the method for detecting heart rate activity executed by the processor 205 of the image-based apparatus 20 for detecting heart rate activity in accordance with an exemplary embodiment. As shown in FIG. 8, step S801 is to obtain color images; step S802 is to perform target area detection; step S803 is to execute image color composition analysis; step S804 is to execute independent component analysis; step S805 is to perform real human determination; Step S806 is to execute physiological information analysis; step S807 is to perform determination of relevance among target areas; and step S808 is to output detection result through the output unit; wherein steps S801, S802, S803, S805, S807, S808 are the same as steps S01, S302, S303, S305, S306, S307, and he descriptions will be omitted.

It should be noted that the filtered signal of each target area obtained in step S804 after completing signal fitness process includes the parameters derived from each filtered signal, including: a signal parameter (regularity parameter) corresponding to each filtered signal, for determining whether each target area as a real human; and a comparison parameter (waveform difference parameter) among the filtered signals, for identifying the relevance among the target areas to determine whether a plurality of target areas belonging to a same baby.

When the image includes a plurality of target areas, after step 805 is used to determine each target area belonging to a real human baby, the relevance between the target area and monitored target can be defined by waveform difference among the filtered signals. In step S806, the relevance analysis module 7056 performs comparison of each filtered signal corresponding to each target area based on a second predefined condition, i.e., waveform difference default value, to identify the relevance among the target areas. It should be noted that the relevance is based on the theory that filtered signals from the same baby should have similar waveform, and filtered signals from different babies should have different waveforms. The waveform here is defined by the time points at which a plurality of peaks of a filtered signal during a specific duration, and therefore a quantitative difference can be obtained by the interval of peaks of a filtered signal, called peak interval parameter. As such, the relevance analysis module 7056 can perform comparison based on the peak interval parameters of two filtered signals to compute the difference of the peak interval parameters among the target areas to obtain the corresponding waveform parameter. Based on a preferred embodiment, the difference between to peak interval parameters corresponding to any two target areas of the target areas is the waveform difference parameter. The computation will continue until the peak interval parameters of all the target areas are completely compared against each other. For example, there are three peak interval parameters for three target areas. After the aforementioned comparison, a waveform difference parameter is obtained for any two peak interval parameters. After completing all the comparison, three waveform difference parameters will be obtained, representing the differences among the three peak interval parameters.

Therefore, based on the comparison between the waveform difference parameter and the waveform difference default value, when the waveform difference parameter generated by two peak interval parameters is less than the waveform difference default value, the two target areas from where the peak interval parameters originate from are determined as relevant. Furthermore, when a waveform difference parameter matches the waveform difference default value of a real human baby, the target areas from where the peak interval parameters originate from are determined as relevant to a real human baby.

Hence, possible scenarios are that a detected color image may include: a plurality of baby areas of a single real human baby (such as, face, hands and feet of a baby, a common scenario in home care), i.e., a plurality of target areas form a single baby; or a single body area form a plurality of real human babies (such as, faces of a plurality babies, a common scenario in hospital or medical institute); or a plurality of baby areas of a plurality of real human babies (such as, face, hands and feet of a plurality of babies, a common scenario in playroom). For the above scenarios of a plurality of target areas, the waveform difference analysis of the relevance analysis module 7056 can be used to determine the relevance of a target area and a certain baby, as well as whether a plurality of target areas belonging to the same baby or different babies. After completing the above step, the processor 205 can issue the analysis instruction based on the result of the above signal determination.

The skin color relevance analysis obtained by the real human determination and the waveform difference comparison disclosed in the embodiments provides further advantages in actual application:
1. Finding various skin colors under various light conditions. A common known approach is to define a wide range of skin colors, which may result in mis-identifying false signal. Because the regularity of each independent component separated from the color image, the apparatus and method for detecting heart rate activity of the present disclosure can eliminate the false signals erroneously identified so as to optimize the skin color range. As the false signals are excluded, the skin color range can be adjusted as more concentrated.
2. Because the waveform difference comparison can correctly group disconnected skin color pixels, the skin color areas of the same person can be grouped together in a scenario of detecting a plurality of persons to reduce interference and improve accuracy of physiological parameters. In addition, when performing head count and human body tracking, a target not facing detection equipment directly or with a facial image can also be correctly counted and tracked to reduce the error.

It should be noted that, in addition to perform physiological information analysis on babies, the aforementioned apparatus and method are also applicable to adults. Other applications include scenarios where facial recognition technique is not suitable, such as, head counts, body tracking, and so on.

Figure 9:
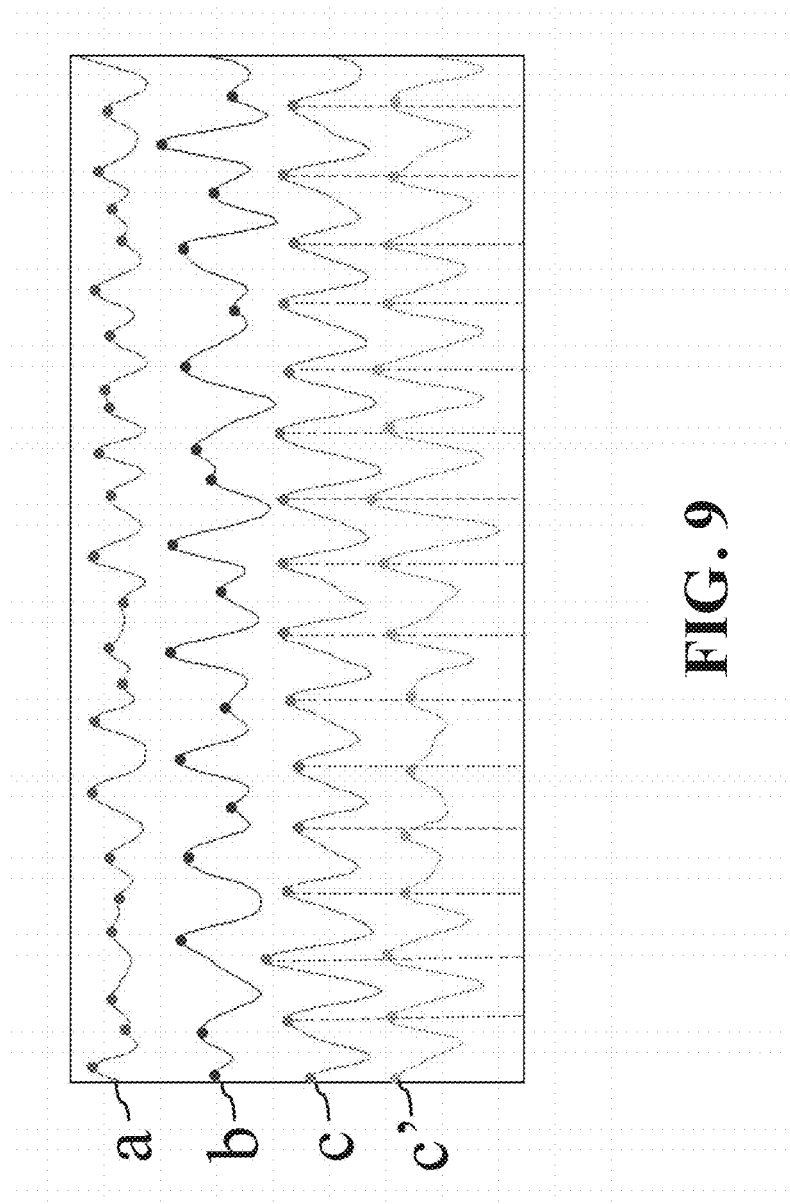
FIG. 9 shows a schematic view of relevance analysis result of the target areas obtained by the second embodiment according to an application scenario.

For the target area relevance analysis executed by the relevance analysis module of the instant embodiment, FIG. 9 shows a schematic view of relevance analysis result of the target areas obtained by the second embodiment according to an application scenario, wherein the application scenario is a day care center, with a skin-color doll A and babies B, C. Both babies B, C are asleep, with faces, hands or feet exposed.

Because the scenario of the instant embodiment needs to perform detection of a plurality of skin color areas, the relevance analysis is performed after determining a skin color area belonging to a real human, which means that when a plurality of skin color areas are determined to belong to real human, any two filtered signals corresponding to the real human signal form a comparison pair, and are compared pair by pair to obtain waveform difference. A quantitative standard of the waveform difference is the peak interval parameter. When a comparison pair has a peak interval parameter less than the waveform difference default value, the two skin color areas of the comparison pair are determined as relevant. Therefore, in a case of plurality of target areas, the waveform difference of the filtered signals can be used to distinguish whether a plurality of skin color areas belong to the same baby. As shown in FIG. 9, the schematic view shows the filtered signal obtained in the scenario of the present embodiment, including a filtered signal a generated by the skin color doll A; a filtered signal b generated by the face of baby B; a filtered signal c generated by the face of baby C; and a filtered signal c' generated by the hand of baby C. Based on the above computation on the filtered signals, the regularity of the filtered signal a is insufficient, thus determined as not real human, and is discarded. After comparing the waveform difference among the filtered signal b generated by the face of baby B, the filtered signal c generated by the face of baby C and the filtered signal c' generated by the hand of baby C, the results are: the peak interval parameter of bc is 3.56, the peak interval parameter of bc' is 3.0, and the peak interval parameter of cc' is 1.13. As the waveform difference default value is 1.5, the processor determines that the filtered signals c, c' having a peak interval parameter (1.13) less than 1.5 as relevant and the two skin color areas belong to the same baby. As such, the above results are used to group the filtered signals and group the filtered signals c, c' as belonging to the same person.

In summary, the image-based method for detecting heart rate activity in the present disclosure is able to achieve real-time monitoring the heart rate activity of targets through obtaining continuous color images and analyzing the heart rate activity of the targets, and is also applicable to monitoring babies with unpredictable postures, as well as eliminating the interference caused by false signals generated by non-real human images. In particular, when detecting a plurality of target areas originating from a plurality of real humans, the relevance among the target areas is identified and determined as belonging to one or more real humans. Through the ability of compute the heart rate activity of a plurality of persons, the accuracy of heart rate activity detection is improved.

An exemplary embodiment describes an image-based method for detecting heart rate activity, including: obtaining a plurality of color images of a monitored target; executing a target area detection process targeting the color images, wherein the target area detection process performing computation analysis on the color images to define a target area in the monitored target in the color image according to a predefined skin color target condition; performing a color image composition analysis on the target area, wherein the color image composition analysis performing statistic computation for a red channel, a green channel and a blue channel of the target area to obtain a red channel signal, a green channel signal and a blue channel signal; based on an independent component analysis method, performing computation on the red channel signal, the green channel signal and the blue channel signal to obtain a first independent component signal, a second independent component signal, and a third independent component signal; performing a frequency domain transform process, a signal energy computation process and a signal fitness process for the first independent component signal, the second independent component signal, and the third independent component signal to obtain a filtered signal; based on a pre-defined condition, performing comparison on the filtered signal to confirm the monitored target as a real human and provide an analysis instruction accordingly; and based on the analysis instruction, executing a physiological information analysis process.

Another embodiment describes an image-based method for detecting heart rate activity, including: obtaining a plurality of color images of a plurality of monitored targets; executing a target area detection process targeting the color images, wherein the target area detection process performing computation analysis on the color images to define a plurality of target areas in the monitored target in the color image according to a predefined skin color target condition; performing a color image composition analysis on each of the plurality of target areas, wherein the color image composition analysis performing statistic computation for a red channel, a green channel and a blue channel of each of the target areas to obtain a red channel signal, a green channel signal and a blue channel signal; based on an independent component analysis method, performing computation on the red channel signal, the green channel signal and the blue channel signal of each of the target areas to obtain a first independent component signal, a second independent component signal, and a third independent component signal; performing a frequency domain transform process, a signal energy computation process and a signal fitness process for the first independent component signal, the second independent component signal, and the third independent component signal of each of the target areas to obtain a filtered signal; based on a first pre-defined condition, performing comparison on the filtered signal of each of the target areas to confirm the filtered signal of each of target areas as a real human signal; based on a second—pre-defined condition, performing comparison respectively on each filtered signal of each of the target areas to identify relevance among each of the target areas to confirm whether each of the target areas belonging to a real human and provide an analysis instruction accordingly; and based on the analysis instruction, executing a physiological information analysis process.

Another exemplary embodiment describes an image-based apparatus for detecting heart rate activity, including: a detecting unit, configured to obtain a plurality of color images of a monitored target; a memory unit, coupled to the detecting unit, configured to store the color images obtained by the detecting unit; and a processor, coupled to the memory unit, wherein the processor further including: a target area defining module, configured to execute a target area detection process targeting the color images, wherein the target area detection process performing computation analysis on the color images to define a target area in the monitored target in the color image according to a predefined skin color target condition; a color image composition analysis module, configured to perform a color image composition analysis on the target area, wherein the color image composition analysis performing statistic computation for a red channel, a green channel and a blue channel of the target area to obtain a red channel signal, a green channel signal and a blue channel signal; an independent component analysis module, based on an independent component analysis method, configured to perform computation on the red channel signal, the green channel signal and the blue channel signal to obtain a first independent component signal, a second independent component signal, and a third independent component signal; a signal processing module, configured to perform a frequency domain transform process, a signal energy computation process and a signal fitness process for the first independent component signal, the second independent component signal, and the third independent component signal to obtain a filtered signal; a comparison module, based on a pre-defined condition, configured to perform comparison on the filtered signal to confirm the monitored target as a real human and provide an analysis instruction accordingly; and a physiological information analysis module, based on the analysis instruction, configured to execute a physiological information analysis process.

Another embodiment describes an image-based apparatus for detecting heart rate activity, including: a detecting unit, configured to obtain a plurality of color images of a plurality of monitored targets; a memory unit, coupled to the detecting unit, configured to store the color images obtained by the detecting unit; a processor, coupled to the memory unit, wherein the processor further including: a target area defining module, configured to execute a target area detection process targeting the color images, wherein the target area detection process performing computation analysis on the color images to define a plurality of target areas in the monitored target in the color image according to a predefined skin color target condition; a color image composition analysis module, configured to perform a color image composition analysis on each of the plurality of target areas, wherein the color image composition analysis performing statistic computation for a red channel, a green channel and a blue channel of each of the target areas to obtain a red channel signal, a green channel signal and a blue channel signal; an independent component analysis module, based on an independent component analysis method, configured to perform computation on the red channel signal, the green channel signal and the blue channel signal of each of the target areas to obtain a first independent component signal, a second independent component signal, and a third independent component signal; a signal processing module, configured to perform a frequency domain transform process, a signal energy computation process and a signal fitness process for the first independent component signal, the second independent component signal, and the third independent component signal of each of the target areas to obtain a filtered signal; a comparison module, based on a first pre-defined condition, configured to perform comparison on the filtered signal of each of the target areas to confirm the filtered signal of each of target areas as a real human signal; a relevance analysis module, based on a second pre-defined condition, configured to perform comparison respectively on each filtered signal of each of the target areas to identify relevance among each of the target areas to confirm whether each of the target areas belonging to a real human and provide an analysis instruction accordingly; and a physiological information analysis module, based on the analysis instruction, configured to execute a physiological information analysis process.

Therefore, the objectives can be achieved through the techniques disclosed by the image-based apparatus and method for detecting heart rate activity.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. An image-based apparatus for detecting heart rate activity, comprising:
  a detecting unit, configured to obtain a plurality of color images of a monitored target;
  a memory unit, coupled to the detecting unit, configured to store the color images obtained by the detecting unit; and
  a processor, coupled to the memory unit, wherein the processor further comprising:
    a target area defining module, configured to execute a target area detection process targeting the color images, wherein the target area detection process performing computation analysis on the color images to define a target area in the monitored target in the color image according to a predefined skin color target condition;
    a color image composition analysis module, configured to perform a color image composition analysis on the target area, wherein the color image composition analysis performing statistic computation for a red channel, a green channel and a blue channel of the target area to obtain a red channel signal, a green channel signal and a blue channel signal;
    an independent component analysis module, based on an independent component analysis method, configured to perform computation on the red channel signal, the green channel signal and the blue channel signal to obtain a first independent component signal, a second independent component signal, and a third independent component signal;
    a signal processing module, configured to perform a frequency domain transform process, a signal energy computation process and a signal fitness process for the first independent component signal, the second independent component signal, and the third independent component signal to obtain a filtered signal;
    a comparison module, configured to compare the filtered signal with at least a pre-defined condition to confirm the monitored target as a real human and provide an analysis instruction accordingly; and
    a physiological information analysis module, based on the analysis instruction, configured to execute a physiological information analysis process,
  wherein the signal energy computation process comprises the Euclidean norm.

2. The image-based apparatus for detecting heart rate activity as claimed in claim 1, wherein the physiological analysis process is to analyze the heart rate activity of the monitored target.

3. The image-based apparatus for detecting heart rate activity as claimed in claim 1, wherein the frequency domain transform process is a Fourier Transform process.

4. The image-based apparatus for detecting heart rate activity as claimed in claim 1, wherein the signal fitness process further comprises a smoothing processing method.

5. The image-based apparatus for detecting heart rate activity as claimed in claim 4, wherein the processor is able to obtain a regularity parameter according to the filtered signal.

6. The image-based apparatus for detecting heart rate activity as claimed in claim 5, wherein the pre-defined condition further comprises a regularity default value.

7. The image-based apparatus for detecting heart rate activity as claimed in claim 6, wherein the monitored target is determined as a real human when the regularity parameter is greater than the regularity default value.

8. An image-based apparatus for detecting heart rate activity, comprising:
  a detecting unit, configured to obtain a plurality of color images of a plurality of monitored targets;
  a memory unit, coupled to the detecting unit, configured to store the color images obtained by the detecting unit; and
  a processor, coupled to the memory unit, wherein the processor further comprising:
    a target area defining module, configured to execute a target area detection process targeting the color images, wherein the target area detection process performing computation analysis on the color images to define a plurality of target areas in the monitored target in the color image according to a predefined skin color target condition;
    a color image composition analysis module, configured to perform a color image composition analysis on each of the plurality of target areas, wherein the color image composition analysis performing statistic computation for a red channel, a green channel and a blue channel of each of the target areas to obtain a red channel signal, a green channel signal and a blue channel signal;
    an independent component analysis module, based on an independent component analysis method, configured to perform computation on the red channel signal, the green channel signal and the blue channel signal of each of the target areas to obtain a first independent component signal, a second independent component signal, and a third independent component signal;
    a signal processing module, configured to perform a frequency domain transform process, a signal energy computation process and a signal fitness process for the first independent component signal, the second independent component signal, and the third independent component signal of each of the target areas to obtain a filtered signal;

a comparison module, configured to compare the filtered signal of each of the target areas with a first pre-defined condition to confirm the filtered signal of each of target areas as a real human signal;

a relevance analysis module, configured to compare each filtered signal of each of the target areas with a second pre-defined condition to identify relevance among each of the target areas to confirm whether each of the target areas belonging to a real human and provide an analysis instruction accordingly; and a physiological information analysis module, based on the analysis instruction, configured to execute a physiological information analysis process, wherein the signal energy computation process comprises the Euclidean norm.

9. The image-based apparatus for detecting heart rate activity as claimed in claim 8, wherein the physiological analysis process is to analyze the heart rate activity of the plurality of monitored targets.

10. The image-based apparatus for detecting heart rate activity as claimed in claim 8, wherein the frequency domain transform process is a Fourier Transform process.

11. The image-based apparatus for detecting heart rate activity as claimed in claim 8, wherein the signal fitness process further comprises a smoothing processing method.

12. The image-based apparatus for detecting heart rate activity as claimed in claim 11, wherein the first pre-defined condition is a regularity default value.

13. The image-based apparatus for detecting heart rate activity as claimed in claim 12, wherein the processor is able to obtain a regularity parameter according to each filtered signal of each target area.

14. The image-based apparatus for detecting heart rate activity as claimed in claim 13, wherein the filtered signal is determined as a real human signal when the regularity parameter of the target area is greater than the regularity default value.

15. The image-based apparatus for detecting heart rate activity as claimed in claim 14, wherein the second pre-defined condition is a waveform difference default value.

16. The image-based apparatus for detecting heart rate activity as claimed in claim 15, wherein the processor obtains a peak interval parameter according to computation on the filtered signal of each of the plurality of target areas.

17. The image-based apparatus for detecting heart rate activity as claimed in claim 16, wherein the processor compares the peak interval parameter of each target area and computes difference between any two peak interval parameters of the target areas to obtain a plurality of waveform difference parameters.

18. The image-based apparatus for detecting heart rate activity as claimed in claim 17, wherein the processor determines the target areas are relevant when the waveform difference parameter is less than the waveform difference default value.

19. An image-based method for detecting heart rate activity, comprising:

obtaining a plurality of color images of a monitored target;

executing a target area detection process targeting the color images, wherein the target area detection process performing computation analysis on the color images to define a target area in the monitored target in the color image according to a predefined skin color target condition;

performing a color image composition analysis on the target area, wherein the color image composition analysis performing statistic computation for a red channel, a green channel and a blue channel of the target area to obtain a red channel signal, a green channel signal and a blue channel signal;

based on an independent component analysis method, performing computation on the red channel signal, the green channel signal and the blue channel signal to obtain a first independent component signal, a second independent component signal, and a third independent component signal;

performing a frequency domain transform process, a signal energy computation process and a signal fitness process for the first independent component signal, the second independent component signal, and the third independent component signal to obtain a filtered signal;

comparing the filtered signal with at least a pre-defined condition to confirm the monitored target as a real human and provide an analysis instruction accordingly; and based on the analysis instruction, executing a physiological information analysis process, wherein the signal energy computation process comprises the Euclidean norm.

20. The image-based method for detecting heart rate activity as claimed in claim 19, wherein the physiological analysis process is to analyze the heart rate activity of the monitored target.

21. The image-based method for detecting heart rate activity as claimed in claim 19, wherein the frequency domain transform process is a Fourier Transform process.

22. The image-based method for detecting heart rate activity as claimed in claim 19, wherein the signal fitness process further comprises a smoothing processing method.

23. The image-based method for detecting heart rate activity as claimed in claim 22, wherein the process is able to obtain a regularity parameter according to the filtered signal.

24. The image-based method for detecting heart rate activity as claimed in claim 23, wherein the pre-defined condition further comprises a regularity default value.

25. The image-based method for detecting heart rate activity as claimed in claim 24, wherein the monitored target is determined as a real human when the regularity parameter is greater than the regularity default value.

26. An image-based method for detecting heart rate activity, comprising:

obtaining a plurality of color images of a plurality of monitored targets;

executing a target area detection process targeting the color images, wherein the target area detection process performing computation analysis on the color images to define a plurality of target areas in the monitored target in the color image according to a predefined skin color target condition;

performing a color image composition analysis on each of the plurality of target areas, wherein the color image composition analysis performing statistic computation for a red channel, a green channel and a blue channel of each of the target areas to obtain a red channel signal, a green channel signal and a blue channel signal;

based on an independent component analysis method, performing computation on the red channel signal, the green channel signal and the blue channel signal of each of the target areas to obtain a first independent component signal, a second independent component signal, and a third independent component signal;

performing a frequency domain transform process, a signal energy computation process and a signal fitness process for the first independent component signal, the second independent component signal, and the third independent component signal of each of the target areas to obtain a filtered signal;

comparing the filtered signal of each of the target areas with a first pre-defined condition to confirm the filtered signal of each of target areas as a real human signal;

comparing each filtered signal of each of the target areas with a second pre-defined condition to identify relevance among each of the target areas to confirm whether each of the target areas belonging to a real human and provide an analysis instruction accordingly; and based on the analysis instruction, executing a physiological information analysis process, wherein the signal energy computation process comprises the Euclidean norm.

27. The image-based method for detecting heart rate activity as claimed in claim 26, wherein the physiological analysis process is to analyze the heart rate activity of the plurality of monitored targets.

28. The image-based method for detecting heart rate activity as claimed in claim 26, wherein the frequency domain transform process is a Fourier Transform process.

29. The image-based method for detecting heart rate activity as claimed in claim 26, wherein the signal fitness process further comprises a smoothing processing method.

30. The image-based method for detecting heart rate activity as claimed in claim 29, wherein the first pre-defined condition is a regularity default value.

31. The image-based method for detecting heart rate activity as claimed in claim 30, wherein the processor is able to obtain a regularity parameter according to each filtered signal of each target area.

32. The image-based method for detecting heart rate activity as claimed in claim 31, wherein the filtered signal is determined as a real human signal when the regularity parameter of the target area is greater than the regularity default value.

33. The image-based method for detecting heart rate activity as claimed in claim 32, wherein the second pre-defined condition is a waveform difference default value.

34. The image-based method for detecting heart rate activity as claimed in claim 33, wherein the processor obtains a peak interval parameter according to computation on the filtered signal of each of the plurality of target areas.

35. The image-based method for detecting heart rate activity as claimed in claim 34, wherein the processor compares the peak interval parameter of each target area and computes difference between any two peak interval parameters of the target areas to obtain a plurality of waveform difference parameters.

36. The image-based method for detecting heart rate activity as claimed in claim 35, wherein the processor determines the target areas are relevant when the waveform difference parameter is less than the waveform difference default value.

* * * * *